(12) United States Patent
Yu et al.

(10) Patent No.: US 8,483,825 B2
(45) Date of Patent: Jul. 9, 2013

(54) AV DELAY FEATURES

(75) Inventors: Yinghong Yu, Shoreview, MN (US); Jiang Ding, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 374 days.

(21) Appl. No.: 12/336,064

(22) Filed: Dec. 16, 2008

(65) Prior Publication Data

US 2009/0163970 A1 Jun. 25, 2009

Related U.S. Application Data

(60) Provisional application No. 61/009,063, filed on Dec. 20, 2007.

(51) Int. Cl.
*A61N 1/00* (2006.01)

(52) U.S. Cl.
USPC .................................................. 607/9; 607/25

(58) Field of Classification Search
USPC .......................................... 607/9, 25, 27–28
See application file for complete search history.

(56) References Cited

U.S. PATENT DOCUMENTS

| 5,626,623 | A | 5/1997 | Kieval et al. |
|---|---|---|---|
| 6,144,880 | A | 11/2000 | Ding et al. |
| 6,351,673 | B1 | 2/2002 | Ding et al. |
| 6,360,127 | B1 | 3/2002 | Ding et al. |
| 6,449,510 | B1 | 9/2002 | Albers et al. |
| 6,542,775 | B2 | 4/2003 | Ding et al. |
| 6,622,040 | B2 | 9/2003 | Ding et al. |
| 6,668,194 | B2 | 12/2003 | VanHout |
| 6,684,103 | B2 | 1/2004 | Ding et al. |
| 6,751,504 | B2 | 6/2004 | Fishler |
| 6,792,307 | B1 | 9/2004 | Levine et al. |
| 6,856,836 | B2 | 2/2005 | Ding et al. |
| 6,859,665 | B2 | 2/2005 | Ding et al. |
| 6,871,096 | B2 | 3/2005 | Hill |
| 7,013,176 | B2 | 3/2006 | Ding et al. |
| 7,020,522 | B1 | 3/2006 | Hoijer et al. |
| 7,079,895 | B2 | 7/2006 | Verbeek et al. |
| 7,079,896 | B1 | 7/2006 | Park et al. |
| 7,110,817 | B2 | 9/2006 | Yu et al. |
| 7,123,960 | B2 | 10/2006 | Ding et al. |

(Continued)

FOREIGN PATENT DOCUMENTS

| EP | 1529551 A1 | 5/2005 |
|---|---|---|
| JP | 2007-515225 A | 6/2007 |
| WO | WO-2005/063333 A1 | 7/2005 |

OTHER PUBLICATIONS

"International Application Serial No. PCT/US2008/013765, International Search Report mailed Apr. 6, 2009", 3 pgs.

(Continued)

*Primary Examiner* — Christopher D Koharski
*Assistant Examiner* — Catherine Voorhees
(74) *Attorney, Agent, or Firm* — Schwegman Lundberg & Woessner, P.A.

(57) ABSTRACT

At least one of a left intraventricular conduction defect, a right intraventricular conduction defect, or no intraventricular conduction defect can be detected using received intrinsic cardiac information from a subject, and a first atrioventricular (AV) delay can be calculated using a first relationship if the left intraventricular conduction defect or no intraventricular conduction defect is detected, or a second AV delay can be calculated using a second relationship if the right intraventricular conduction defect is detected.

18 Claims, 6 Drawing Sheets

U.S. PATENT DOCUMENTS

| | | |
|---|---|---|
| 7,181,284 B2 | 2/2007 | Burnes et al. |
| 7,203,540 B2 | 4/2007 | Ding et al. |
| 7,248,925 B2 * | 7/2007 | Bruhns et al. ............... 607/25 |
| RE39,897 E | 10/2007 | Mower |
| 7,310,554 B2 | 12/2007 | Kramer et al. |
| 2002/0077559 A1 | 6/2002 | Ding et al. |
| 2003/0144703 A1 * | 7/2003 | Yu et al. ............... 607/17 |
| 2004/0147966 A1 | 7/2004 | Ding et al. |
| 2005/0131472 A1 | 6/2005 | Ding et al. |
| 2006/0047320 A1 | 3/2006 | Ding et al. |
| 2006/0235481 A1 * | 10/2006 | Fogoros et al. ............... 607/24 |
| 2006/0259086 A1 * | 11/2006 | Yu et al. ............... 607/9 |
| 2006/0276847 A1 | 12/2006 | Yu et al. |
| 2007/0150013 A1 | 6/2007 | Ding et al. |
| 2007/0299477 A1 * | 12/2007 | Kleckner et al. ............... 607/9 |
| 2008/0004665 A1 | 1/2008 | McCabe et al. |

OTHER PUBLICATIONS

"International Application Serial No. PCT/US2008/013765, Written Opinion mailed Apr. 6, 2009", 6 pgs.

"Japanese Application Serial No. 2010-539455, Office Action mailed Apr. 24, 2012", (w/ English Translation), 8 pgs.

"Japanese Application Serial No. 2010-539455, Response filed Aug. 24, 2012 to Office Action mailed Apr. 20, 2012", (w/ English Translation of Amended Claims), 13 pgs.

* cited by examiner

AV DELAY FEATURES

CROSS-REFERENCE TO RELATED APPLICATIONS

This application claims the benefit under 35 U.S.C. 119(e) of U.S. Provisional Application No. 61/009,063, filed on Dec. 20, 2007, which is hereby incorporated by reference in its entirety.

TECHNICAL FIELD

This document pertains generally to implantable medical devices, and more particularly, but not by way of limitation, to atrioventricular (AV) delay features.

BACKGROUND

Cardiac rhythm or function management devices can include implantable devices to help maintain heart rhythm or function. Cardiac rhythm or function management devices can include pacers, defibrillators, cardioverters, cardiac resynchronization therapy (CRT), or various combinations of these or other devices. In various examples, cardiac rhythm or function management devices can sense intrinsic heart contractions, deliver pacing pulses to evoke responsive heart contractions, or deliver a shock to interrupt certain arrhythmias. In certain examples, one or more of these functions can help improve a patient's heart rhythm or can help coordinate a spatial nature of a heart contraction, either of which can improve cardiac output of blood to help meet the patient's metabolic need for such cardiac output.

OVERVIEW

In an example, at least one of a left intraventricular conduction defect, a right intraventricular conduction defect, or no intraventricular conduction defect can be detected using received intrinsic cardiac information from a subject. In certain examples, a first atrioventricular (AV) delay can be calculated using a first relationship if the left intraventricular conduction defect or no intraventricular conduction defect is detected. In other examples, a second AV delay can be calculated using a second relationship if the right intraventricular conduction defect is detected.

In Example 1, a system includes an implantable medical device and a processor. The implantable medical device is configured to receive intrinsic cardiac information from a subject, the implantable medical device including at least one of an atrial sensing channel configured to receive an intrinsic atrial activation, a left ventricular sensing channel configured to receive an intrinsic left ventricular activation, or a right ventricular sensing channel configured to receive an intrinsic right ventricular activation. The processor is configured to detect at least one of a left intraventricular conduction defect, a right intraventricular conduction defect, or no intraventricular conduction defect using the intrinsic cardiac information, to calculate a first atrioventricular (AV) delay using a first relationship if the left intraventricular conduction defect or no intraventricular conduction defect is detected, and to calculate a second AV delay using a second relationship if the right intraventricular conduction defect is detected.

In Example 2, the first relationship of Example 1 optionally includes a relationship between a right intrinsic atrioventricular interval ($AV_R$) and a ventricular depolarization duration (QRS).

In Example 3, the relationship between the $AV_R$ and the QRS of any one or more of Examples 1-2 optionally includes: $k_1 AV_R + k_2 QRS + k_3$, wherein $k_1$, $k_2$, and $k_3$ are coefficients derived from an analysis of clinical population data relating measured $AV_R$, QRS, and a known AV delay.

In Example 4, the QRS of any one or more of Examples 1-3 optionally includes at least one of a user-input value including a measured width of a QRS complex or an intrinsic interventricular interval ($\Delta_{RL}$).

In Example 5, the first relationship of any one or more of Examples 1-4 optionally includes a relationship between a right intrinsic atrioventricular interval ($AV_R$) and a left intrinsic atrioventricular interval ($AV_L$).

In Example 6, the relationship between the $AV_R$ and the $AV_L$ of any one or more of Examples 1-5 optionally includes: $k_4 AV_R + k_5 AV_L + k_6$, wherein $k_4$, $k_5$, and $k_6$ are coefficients derived from an analysis of clinical population data relating measured $AV_R$, $AV_L$, and a known AV delay.

In Example 7, the processor of any one or more of Examples 1-6 is optionally configured to determine a first occurring intrinsic atrioventricular interval (AVI), and wherein the second relationship of any one or more of Examples 1-6 optionally includes a function of the AVI.

In Example 8, the function of the AVI of any one or more of Examples 1-7 optionally includes:
$k_7 \times AVI$, wherein $k_7$ includes at least one of a user-specified value or a value derived from an analysis of clinical population data relating a measured AVI and a known AV delay.

In Example 9, the left intraventricular conduction defect of any one or more of Examples 1-8 optionally includes a left bundle branch block (LBBB) and the right intraventricular conduction defect includes a right bundle branch block (RBBB).

In Example 10, the intrinsic cardiac information of any one or more of Examples 1-9 optionally includes at least one of an intrinsic atrioventricular interval ($AV_R$) determined using the received intrinsic atrial activation and the received intrinsic right ventricular activation, an intrinsic atrioventricular interval ($AV_L$) determined using the received intrinsic atrial activation and the received intrinsic left ventricular activation, a measured width or a duration of a QRS wave, an intrinsic interventricular interval ($\Delta_{RL}$) determined using the received intrinsic left ventricular activation and the received intrinsic right ventricular activation, or a first occurring intrinsic atrioventricular interval (AVI) determined using the received intrinsic atrial activation, the received intrinsic left ventricular activation, and the received intrinsic right ventricular activation.

In Example 11, a method includes receiving intrinsic cardiac information from a subject including at least one of an intrinsic atrial activation, an intrinsic left ventricular activation, or an intrinsic right ventricular activation, detecting at least one of a left intraventricular conduction defect, a right intraventricular conduction defect, or no intraventricular conduction defect using the intrinsic cardiac information, calculating a first atrioventricular (AV) delay using a first relationship if the left intraventricular conduction defect or no intraventricular conduction defect is detected, and calculating a second AV delay using a second relationship if the right intraventricular conduction defect is detected.

In Example 12, the calculating the first relationship of Example 11 optionally includes using a relationship between a right intrinsic atrioventricular interval ($AV_R$) and a ventricular depolarization duration (QRS).

In Example 13, the using the relationship between the right intrinsic atrioventricular interval ($AV_R$) and the ventricular depolarization duration (QRS) of any one or more of Examples 11-12 optionally includes using:

$k_1 AV_R + k_2 QRS + k_3$, wherein $k_1$, $k_2$, and $k_3$ are coefficients derived from an analysis of clinical population data relating measured $AV_R$, QRS, and a known AV delay.

In Example 14, the using the QRS of any one or more of Examples 11-13 optionally includes using at least one of a user-input value including a measured width of a QRS complex or an intrinsic interventricular interval ($\Delta_{RL}$).

In Example 15, the calculating the first relationship of any one or more of Examples 11-14 optionally includes using a relationship between a right intrinsic atrioventricular interval ($AV_R$) and a left intrinsic atrioventricular interval ($AV_L$).

In Example 16, the using the relationship between the $AV_R$ and the $AV_L$, of any one or more of Examples 11-15 optionally includes using:

$k_4 AV_R + k_5 AV_L + k_6$, wherein $k_4$, $k_5$, and $k_6$ are coefficients derived from an analysis of clinical population data relating measured $AV_R$, $AV_L$, and a known AV delay.

In Example 17, the method of any one or more of Examples 11-16 optionally includes determining a first occurring intrinsic atrioventricular interval (AVI), and the using the second relationship of any one or more of Examples 11-16 optionally includes using a function of the AVI.

In Example 18, the using the function of the AVI of any one or more of Examples 11-17 optionally includes using:

$k_7 \times AVI$, wherein $k_7$ includes at least one of a user-specified value or a value derived from an analysis of clinical population data relating a measured AVI and a known AV delay.

In Example 19, the detecting the right intraventricular conduction defect of any one or more of Examples 11-18 optionally includes detecting a left bundle branch block (LBBB), and the detecting the left intraventricular conduction defect of any one or more of Examples 11-18 optionally includes detecting a right bundle branch block (RBBB).

In Example 20, the using the intrinsic cardiac information of any one or more of Examples 11-19 optionally includes using at least one of an intrinsic atrioventricular interval ($AV_R$) determined using the received intrinsic atrial activation and the received intrinsic right ventricular activation, an intrinsic atrioventricular interval ($AV_L$) determined using the received intrinsic atrial activation and the received intrinsic left ventricular activation, a measured width or a duration of a QRS wave, an intrinsic interventricular interval ($\Delta_{RL}$) determined using the received intrinsic left ventricular activation and the received intrinsic right ventricular activation, or a first occurring intrinsic atrioventricular interval (AVI) determined using the received intrinsic atrial activation, the received intrinsic left ventricular activation, and the received intrinsic right ventricular activation.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Generally, heart failure (HF) refers to a cardiac disorder that impairs the ability of a heart to pump a sufficient amount of blood through a body. HF can be due to a variety of etiologies, e.g., ischemic heart disease. Certain HF subjects suffer from some degree of AV block such that their cardiac output can be improved by synchronizing atrial and ventricular contractions using dual chamber pacing having a specified atrioventricular (AV) delay interval. Dual chamber pacing can include pacing where energy is delivered to both at least one atrium and at least one ventricle. The AV delay interval, as used herein, refers to the interval between an atrial event (e.g., an atrial pace or an atrial sense, usually the right atrium) and a first ventricular pace to one of the ventricles (e.g., a right ventricle) during the same cardiac cycle. The AV delay interval can be the same or different depending upon whether it is initiated by an atrial sense or an atrial pace (e.g., in atrial tracking mode or AV sequential pacing mode, respectively). Bi-ventricular pacing includes pacing both the left ventricle and the right ventricle. The biventricular offset (BVO) interval, as used herein, refers to the interval between the first ventricular pace and a second ventricular pace to the other ventricle (e.g., the left ventricle) during the same cardiac cycle. One approach to bi-ventricular pacing includes specifying an AV delay interval and a BVO interval. Another approach to bi-ventricular pacing includes specifying a separate AV delay interval for each ventricle, which can be designated as $AV_R$ for the right ventricle and $AV_L$ for the left ventricle. In subjects having normal AV conduction, the optimal or desired AV delay and BVO intervals can be related to both the intrinsic atrioventricular interval and the amount of pre-excitation time needed for one ventricle relative to the other (e.g., the extent of the ventricular conduction deficit).

Figure 1:
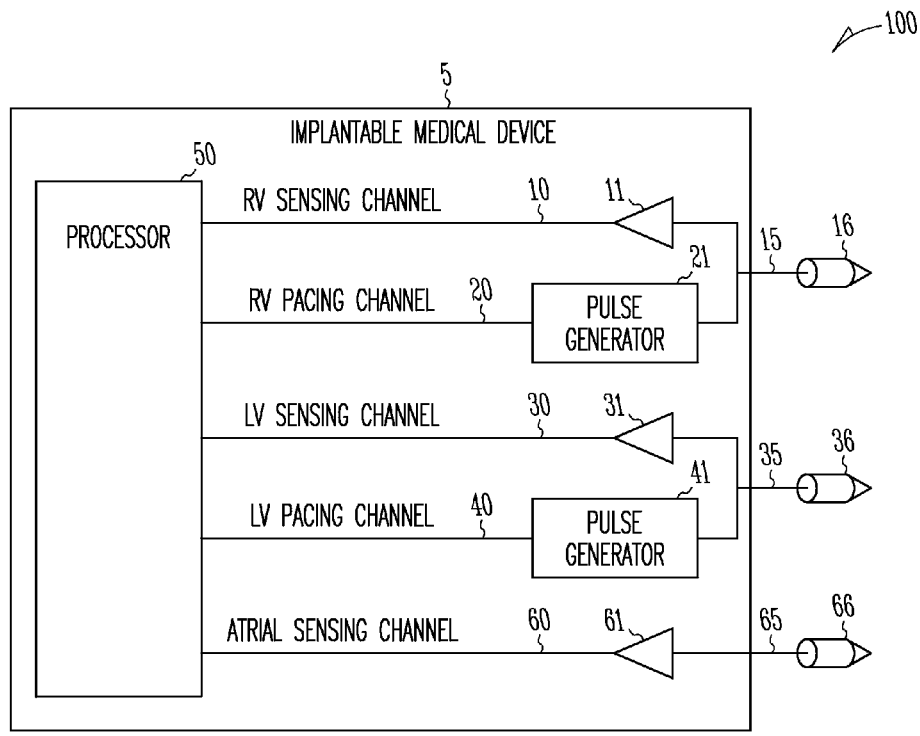
FIGS. 1, 2, and 4 illustrate generally examples of systems or portions of a system for delivering cardiac therapy.

FIG. 1 illustrates generally an example of a system 100 for delivering cardiac therapy. In an example, the system 100 can include an implantable medical device (IMD) 5 having a processor 50, a right ventricular sensing channel 10, a right ventricular pacing channel 20, a left ventricular sensing channel 30, a left ventricular pacing channel 40, and an atrial sensing channel 60. The atrial sensing channel 60 can include at least one of a right atrial sensing channel or a left atrial sensing channel. In other examples, the IMD 5 can include a combination of at least one of the [[a]] right ventricular sensing channel 10, the right ventricular pacing channel 20, the left ventricular sensing channel 30, the left ventricular pacing channel 40, or the atrial sensing channel 60.

In certain examples, the right ventricular sensing channel 10 can include a sense amplifier 11, the left ventricular sensing channel 30 can include a sense amplifier 31, the right ventricle pacing channel 20 can include a pulse generator 21, the left ventricular pacing channel 40 can include a pulse generator 41, and the atrial sensing channel 60 can include a sense amplifier 61. In other examples, the right ventricular sensing channel 10 or the right ventricular pacing channel 20 can be coupled to an electrode 16 disposed on a lead 15 or elsewhere, the left ventricular sensing channel 30 or the left ventricular pacing channels 40 can be coupled to an electrode 36 disposed on a lead 35 or elsewhere, or the atrial sensing channel 60 can be coupled to an electrode 66 disposed on a lead 65 or elsewhere.

In certain examples, the lead 15 can be configured to electrically couple the sense amplifier 11 or the pulse generator 21 to the electrode 16, which can be configured to be located in a right ventricle, such as in the septal region, the free wall region, or another region of the right ventricle. Similarly, the lead 35 can be configured to electrically couple the sense amplifier 31 or the pulse generator 41 to the electrode 36, which can be configured to be located in, on, or near a left ventricle, such as in the septal region, the free wall region, or another region of the left ventricle or in the coronary vasculature. Further, the lead 65 can be configured to electrically couple the sense amplifier 61 to the electrode 66, which can be configured to be located in at least one of a right atrium or a left atrium of the subject 101.

In the example of FIG. 1, the processor 50 can be an implantable component, an external component, or a combination or permutation of an implantable processor and an external processor. In an example, the processor 50 can be configured to compute an AV delay. In certain examples, if at least a portion of the processor 50 includes an external processor, then the processor 50 can be configured to be communicatively coupled (such as via telemetry, RF, or other communication protocol) with the remaining implantable components (such as the sense amplifier 11, 31, the pulse generator 21, 41, the lead 15, 35, or the electrode 16, 36). In an example, the implantable processor can be configured to have reduced or minimal functionality or power consumption. In certain examples, it can be advantageous for the processor 50 to include an external processor for computing complex operations, such as to compute an AV delay interval. In other examples, the external processor can include an external device that can be either local or remote. In an example, the processor 50 can include a microcontroller, a microprocessor, a logic circuit, or other processor.

Figure 2:
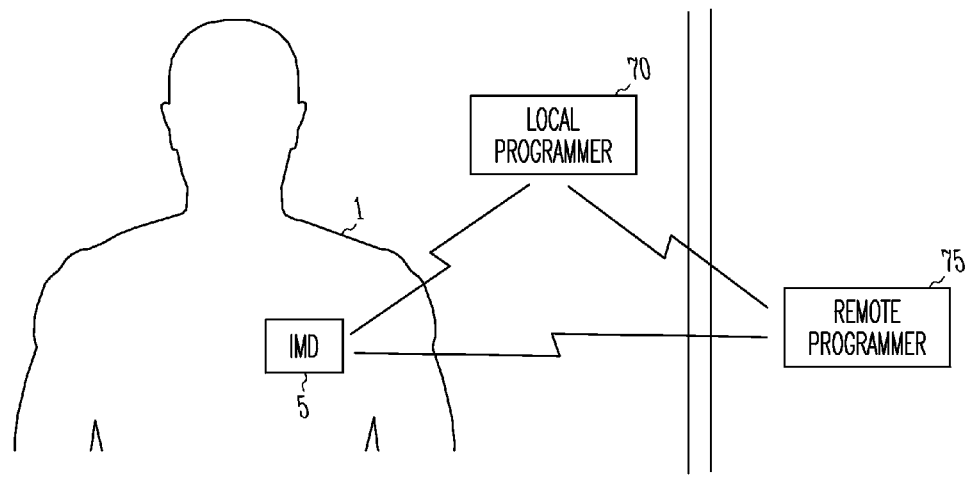

FIG. 2 illustrates generally an example of a portion of a system 200 including an IMD 5 configured to be implanted in a subject 101. The system 200 can include at least one of a local user interface 70 or a remote user interface 75. Both the local user interface 70 and the remote user interface 75 are external components and can be used to, among other things, program, or otherwise communicate with, the IMD 5. In an example, the local user interface 70 can include a hand-held user interface or other user interface capable of being positioned in communication proximity to the processor 50. The proximity range between the processor 50 and the local user interface 70 can vary depending upon the type of data communication and is bound by the physical constraints of the communication type. In an example, the remote user interface 75 can include any user interface configured to communicate with the IMD 5 either directly or indirectly (such as through another device, e.g., a router, the local user interface 70, etc.). In various examples, the remote user interface 75 can be configured to communicate with or store information from a plurality of implanted or external devices, and the remote user interface 75 can be configured to be located a long distance from the subject 1.

In an example, the local user interface 70 or the remote user interface 75 can be configured to send information to or receive information from the IMD 5. The information can include programming information, subject data, device data, or other instructions, alerts, or other information. Further, the local user interface 70 or the remote user interface 75 can be configured to communicate the sent or received information to a user or physician, such as by sending an alert via email of the status of the subject 1 or the system components.

AV Delay Calculation Depending on Left or Right Bundle Branch Block

Some HF subjects suffer from intraventricular conduction defects, or bundle branch blocks. In an example, if a first side of the heart (e.g., the left side or alternatively the right side) has become enlarged due to HF, the ventricular intrinsic heart signals may travel through and depolarize the first side of the heart more slowly than in a second side of the heart (e.g., the right side or alternatively the left side). As a result, the ventricles do not contract simultaneously, but rather, contract with one ventricle trailing or leading the other ventricle, which can reduce the pumping efficiency of the heart.

Bundle branch block typically refers to left bundle branch block (LBBB), where the conduction defect resides in the left side of the heart, or right bundle branch block (RBBB), where the conduction defect resides in the right side of the heart. The cardiac output of subjects suffering from intraventricular conduction defects (e.g., LBBB or RBBB) can be increased by improving the synchronization of right and left ventricular contractions with biventricular pacing.

Figure 3:
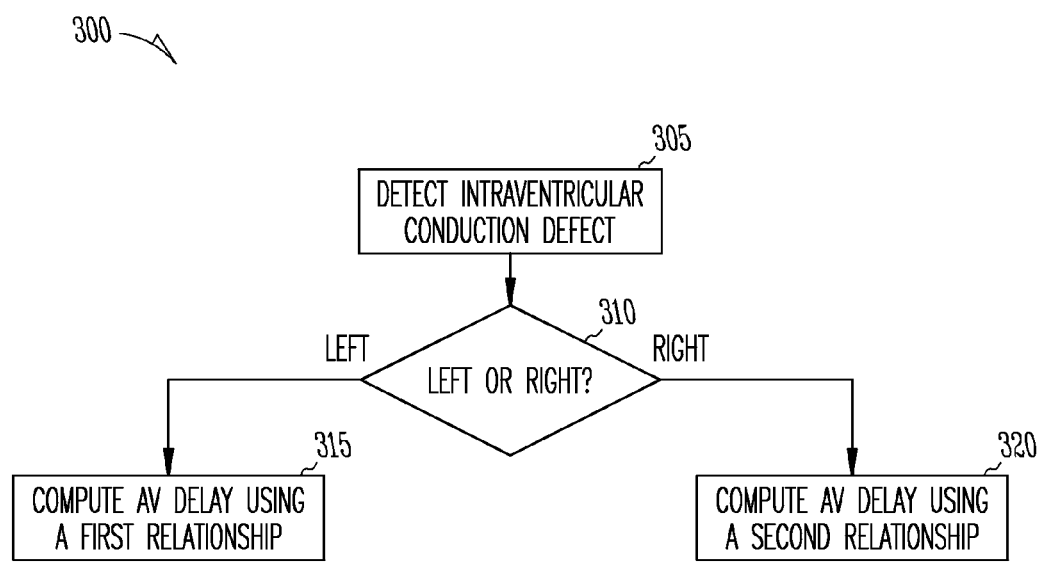
FIG. 3 illustrates generally an example of a method for computing an AV delay dependant upon a detected left or right intraventricular conduction defect.

FIG. 3 illustrates generally an example of a method 300 for computing an AV delay that is dependent upon the existence or a degree of a detected left or right intraventricular conduction defect, e.g., LBBB or RBBB. Generally, calculating an AV delay that is dependent upon the existence or a degree of detected left or right intraventricular conduction defect can lead to an improved synchronization of the right and left ventricular contractions depending on the type or degree of intraventricular conduction defect, which in turn can lead to an increased cardiac output.

At 305, an intraventricular conduction defect is detected. In certain examples, the intraventricular conduction defect can be detected using at least one detected intrinsic ventricular timing. In certain examples, the intraventricular conduction defect can be detected using at least one of the atrial sensing channel 60, the LV sensing channel 30, or the RV sensing channel 10. Further, the intraventricular conduction defect can be detected using a left intrinsic atrioventricular interval ($AV_L$) measured as the interval between an atrial sense or pace and a left ventricular sense, a right intrinsic atrioventricular interval ($AV_R$) measured as the interval between an atrial sense or pace and a right ventricular sense, an intrinsic interventricular conduction delay between the right and left ventricles ($\Delta_{RL}$) (in certain examples, the $\Delta_{RL}$ can be used as a proxy for the width of a QRS wave, which is indicative of the duration of the subject's ventricular depolarization), or other intrinsic or paced timing intervals. In other examples, the intraventricular conduction defect can be detected using a measured QRS complex duration and $\Delta_{RL}$. In an example, an intraventricular conduction defect can be detected using the width of the QRS complex (e.g., if the QRS complex is longer than 120 ms). In other examples, the intraventricular conduction defect can be detected and classified as a left conduction defect (e.g., LBBB) or a right conduction defect (e.g., RBBB) using the $\Delta_{RL}$, or the difference between the $AV_L$ and the $AV_R$.

In an example, the intraventricular conduction defect can be detected using a detected timing relationship between an intrinsic right or left electrogram recording, such as disclosed in the commonly assigned Ding et al. U.S. Pat. No. 6,622,040 entitled, "AUTOMATIC SELECTION OF STIMULATION CHAMBER FOR VENTRICULAR RESYNCHRONIZATION THERAPY," (herein "the Ding et al. '040 patent") the disclosure of which is incorporated by reference in its entirety, including its disclosure of determining QRS complex duration or right or left ventricular depolarizations. In other examples, other methods of detecting conduction defect can be used, such as by detecting an intrinsic interventricular conduction delay between the right ventricular sense and the left ventricular sense ($\Delta_{RL}$) (e.g., as a proxy for the determining the duration of the QRS complex).

At 310, the detected intraventricular conduction defect is determined to be one of a left conduction defect (e.g., LBBB) or a right conduction defect (RBBB). In certain examples, the determination of whether LBBB or RBBB exists can be complete at step 305. In an example, if neither LBBB or RBBB exist, then process flow can continue as if LBBB exists. In other examples, the left or right conduction defect can be determined using intrinsic ventricular timings, either alone or in combination with the detected intraventricular conduction defect information from step 305, such as that disclosed in the above-incorporated Ding et al. '040 patent, or the left or right conduction defect can be determined using at least one other intrinsic ventricular timing.

If, at 310, the detected intraventricular conduction defect is determined to be a left intraventricular conduction defect (or if no intraventricular conduction defect is determined), then, at 315, an AV delay is computed using a first relationship. In an example, the first relationship can include desired or optimal AV delay calculation, such as disclosed in the commonly assigned Ding et al. U.S. Pat. No. 7,013,176 entitled, "METHOD AND APPARATUS FOR SETTING PACING PARAMETERS IN CARDIAC RESYNCHRONIZATION THERAPY," (herein "the Ding et al. '176 patent") the commonly assigned Ding et al. U.S. Pat. No. 7,203,540 entitled, "METHOD AND SYSTEM FOR SETTING CARDIAC RESYNCHRONIZATION THERAPY PARAMETERS," (herein "the Ding et al. '540 patent") or the commonly assigned Ding et al. U.S. Pat. No. 7,123,960 entitled, "METHOD AND SYSTEM FOR DELIVERING CARDIAC RESYNCHRONIZATION THERAPY WITH VARIABLE ATRIO-VENTRICULAR DELAY," (herein "the Ding et al. '960 patent") the disclosures of which are each incorporated by reference in their entirety, including their disclosure of computing an optimal or desired AV delay interval. In an example in which the detected intraventricular conduction defect is determined to be a left intraventricular conduction defect, the first relationship can include a relationship between the AV delay interval, a right intrinsic atrioventricular interval, and a ventricular depolarization duration (e.g., $AVD=k_1 AV_R + k_2 QRS + k_3$, where QRS is the ventricular depolarization duration (e.g., the width of the QRS wave) and $k_1$, $k_2$, and $k_3$ are coefficients, such as can be derived from an analysis of clinical population data relating AVD, $AV_R$, and QRS). In an example, the width of the QRS wave can be determined, for example, by a clinician, and can be input manually (e.g., into the processor 5, the local user interface 70, etc.). In certain examples, a detected intraventricular conduction delay (e.g., $\Delta_{RL}$) can be used as a proxy for the width of the QRS wave. In another example in which the detected intraventricular conduction defect is determined to be a left intraventricular conduction defect, the first relationship can include a relationship between the AV delay interval, a right intrinsic atrioventricular interval, and a left intrinsic atrioventricular interval (e.g., $AVD=k_4 AV_R + k_5 AV_L + k_6$, where $k_4$, $k_5$, and $k_6$ are coefficients, such as can be derived from an analysis of clinical population data relating AVD, $AV_R$, and $AV_L$). In other examples, other calculations can be used for the first relationship.

If, at 310, the detected intraventricular conduction defect is determined to be a right intraventricular conduction defect, then, at 320, an AV delay is computed using a second relationship. In an example, the second relationship can include a function of a detected intrinsic AV interval (AVI). In an example, the intrinsic AVI can be detected as the interval between an atrial event and an RV depolarization, an LV depolarization, or the ventricle having the first intrinsic depolarization following the atrial event. In an example, the function can include a percentage (e.g., 70%, 75%, etc.) of the AVI, such that the relationship can be described as $k_7 \times AVI$, wherein $k_7$ includes at least one of a user-specified value, such as a manufacturer-specified number or a number input by a clinician, a number calculated using, or correlated to, physiological data from the subject (e.g., using intrinsic or paced timing intervals or other physiological data) and set to produce an AV delay configured to increase the hemodynamic function of the heart, or a value derived from an analysis of clinical population data relating a measured AVI and a known AV delay.

AV Delay Calculation Depending on Selected Lead Location

Figure 4:
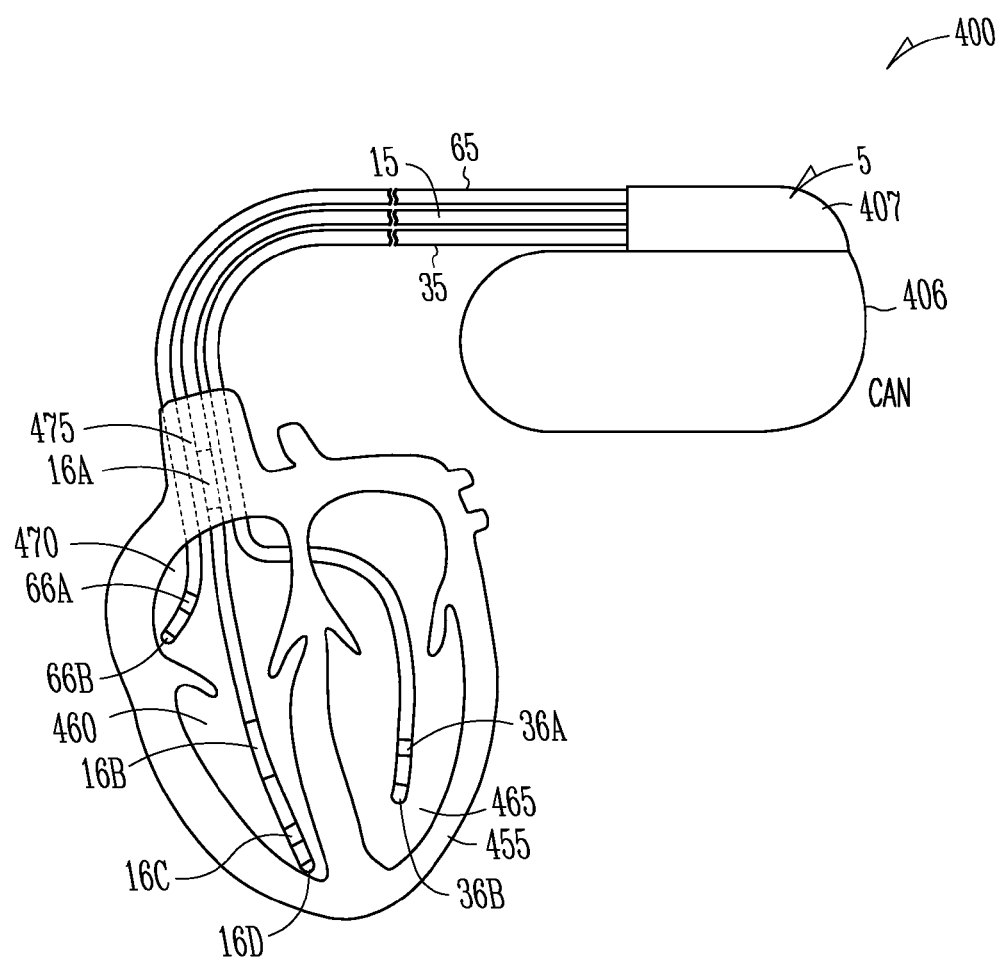

FIG. 4 illustrates generally an example of portions of a system 400 including an IMD 5, an RV lead 15, a LV lead 35, an atrial lead 65, and a heart 455. The IMD 5 can include a housing 406 (or can), and a header 407. In an example, at least a portion of the exterior of the housing 406 can include an electrode, herein referred to as the can electrode. The RV lead 15 can include a first electrode 16a configured to be located in the superior vena cava 475 of the heart 455, and a second electrode 16b, a third electrode 16c and a fourth electrode 16d configured to be located in the right ventricle 460 of the heart 455. The LV lead 35 can include a fifth electrode 36a and a sixth electrode 36b configured to be located in, on, or near the left ventricle 465 of the heart 455, such as within the coronary vasculature, near the left ventricular free wall, or near the left ventricular anterior wall. The atrial lead 65 can include a seventh electrode 66a and an eighth electrode 66b configured to be located in the right atrium 470 of the heart 455. In certain examples, the can electrode can be electrically coupled to at least one other electrode (e.g., the first electrode 16a), or the can electrode can be electrically isolated from other electrodes and capable of independent control. Further, in certain examples, the first electrode 16a through the eighth electrode 66b can include at least one of a coil-type electrode, a ring-type electrode, or a tip electrode.

In certain examples, the RV lead 15 can be configured to electrically couple the IMD 5 to at least one of the right ventricle 460, the right atrium 470, or the superior vena cava 475 using at least one electrode (e.g., the first electrode 16a, the second electrode 16b, the third electrode 16c, or the fourth electrode 16d), the LV lead 35 can be configured to electrically couple the IMD 5 to the left ventricle 465 using at least one electrode (e.g., the fifth electrode 36a or the sixth electrode 36b), or the atrial lead 65 can be configured to electrically couple the IMD 5 to the right ventricle 470 using at least one electrode (e.g., the seventh electrode 66a or the eighth electrode 66b). In an example, at least one of the second electrode 16b, the third electrode 16c, or the fourth electrode 16d can be configured to be located in, on, or near a right apical region of the heart 455. In other examples, the fifth electrode 36a or the sixth electrode 36b can be configured to be located in, on, or near a left apical region of the heart 455 or a left ventricular free lateral wall of the heart 455.

Figure 5:
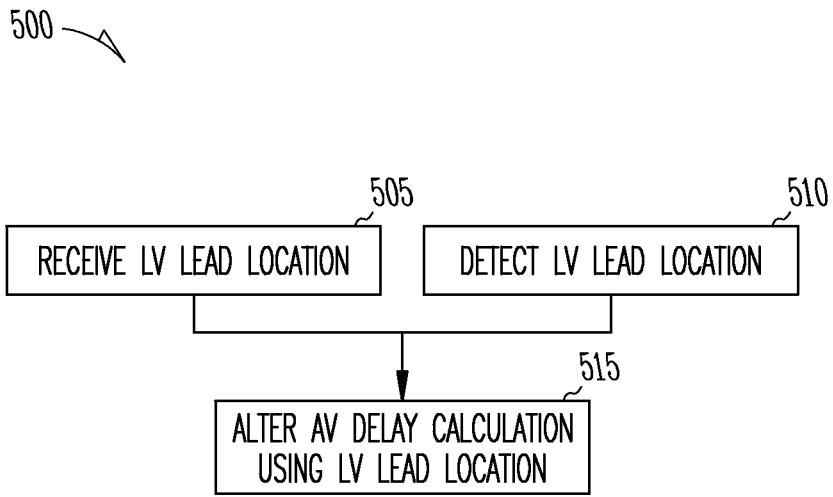
FIG. 5 illustrates generally an example of a method including altering an AV delay calculation using a LV lead location.

FIG. 5 illustrates generally an example of a method 500 including altering an AV delay calculation using information about a LV electrode location (e.g., at or near the LV free wall or the LV anterior wall).

At 505, a LV electrode location information is received, such as from a clinician or other user, from a medical device user interface (e.g., the local user interface 70, the remote user interface 75, etc.). In an example, the processor 5 can be configured to receive the LV electrode location information from a clinician or other user. The LV electrode location information can be input by the clinician or other user during or following implantation of the LV lead, e.g., the LV lead 35. In other examples, medical imaging or other techniques can be used by the clinician or other user to estimate the LV electrode location. Once the LV electrode location is estimated, the clinician or other user can input the LV electrode location information to the processor 5.

At 510, the LV electrode location is detected. In an example, the LV electrode location can be detected or estimated using LV lead measurements. In certain examples, the LV electrode location can be detected or estimated, such as by using a measured lead impedance, using a detected time interval (e.g., the AVI, the $AV_R$, $AV_L$, etc.), using a combination of more than one detected time interval (e.g., $\Delta_{RL}$, etc.), or using a comparison or combination of any one or more of the above LV lead measurements. Generally, the delay between a reference time and sensed activation at the LV electrode will be greater if the LV electrode is located at or near the free wall of the LV rather than at or near the anterior wall. In an example, if the delay between the reference time (e.g., a sensed activation at the RV electrode, an onset of the QRS wave, etc.) and the sensed activation at the LV electrode is above a threshold (e.g., a predetermined threshold, an absolute threshold, a population threshold, a subject-specific threshold, etc.), then the LV electrode can be determined to be located at the free wall of the left ventricle. In other examples, if the delay between the reference time and the sensed activation at the LV electrode is below a threshold, then the LV electrode can be determined to be located at the anterior wall of the left ventricle.

At 515, the AV delay calculation is altered using the LV electrode location, such as by computing or altering the AV delay calculation depending upon the LV electrode location (e.g., a LV electrode location of the free wall or the anterior wall). In an example, if the LV electrode location information is received at 505, then the AV delay calculation can be altered using the received LV electrode location information. In another example, if the LV electrode location is detected or estimated at 510, then the AV delay calculation can be altered using the detected LV electrode location. In other examples, the LV electrode location information can be received at 505 and detected at 510. If the received LV electrode location is the same as the detected LV electrode location, then the AV delay calculation can be altered using the received and detected LV electrode location. If the received LV electrode location differs from the detected LV electrode location, then a specified one of the received location and the detected location can assume priority and the AV delay calculation can be altered using the location having priority, the AV delay calculation can be altered using the combination of the received location and the detected location, or the AV delay calculation can be left unaltered and an alert can be communicated to the subject, the clinician, or some other user, such as by using the processor 50, the local user interface 70, the remote user interface 75, or a combination of one or more of the processor 50, the local user interface 70, or the remote user interface 75.

In an example, if a LV electrode location is received at 505, then the LV electrode location is not detected at 510. In other examples, if a LV electrode location is detected at 510, then the LV electrode location is not received at 505. In an example, the AV delay can be computed or altered using the AV delay calculation described above. In an example, the at least a portion of the AV delay calculation can be altered depending upon the received or detected LV electrode location, such as one or more of coefficients $k_1$-$k_6$, etc.

In other examples, the AV delay calculation can be altered using a RV electrode location or an atrial electrode location similarly to using the LV electrode location described above.

In Example 1, a system can include an implantable medical device including a processor configured to receive or detect an LV lead or electrode location and to calculate an AV delay using the received or detected LV lead or electrode location.

In Example 2, the processor of Example 1 is optionally configured to alter an AV delay calculation using the received or detected LV lead or electrode location.

In Example 3, a method includes receiving or detecting a LV lead or electrode location and calculating an AV delay using the received or detected LV lead or electrode location.

In Example 4, the calculating the AV delay of Example 3 optionally includes altering an AV delay calculation using the received or detected LV lead or electrode location.

AV Delay Calculation Using First Ventricular Activation

Generally, for a particular cardiac cycle, most subjects exhibit a later intrinsic activation in the left ventricle and an earlier intrinsic activation in the right ventricle. Others, however, exhibit a later intrinsic activation in the right ventricle and an earlier intrinsic activation in the left ventricle. As such, the sequence or order of intrinsic ventricular activations in the left and right ventricle can be determined, such as to more accurately calculate a physiologically appropriate AV delay interval.

In an example, the AV delay can be calculated using an $AV_R$ (e.g., AVD=$k_1 AV_R + k_2 \Delta_{RL} + k_3$). However, the present inventor has recognized, among other things, that if the intrinsic right ventricular activation occurs later than the intrinsic left ventricular activation, that computing the AV delay using the $AV_L$ (e.g., AVD=$k_1 AV_L + k_2 \Delta_{RL} + k_3$) can increase the hemodynamic function of the heart.

Figure 6:
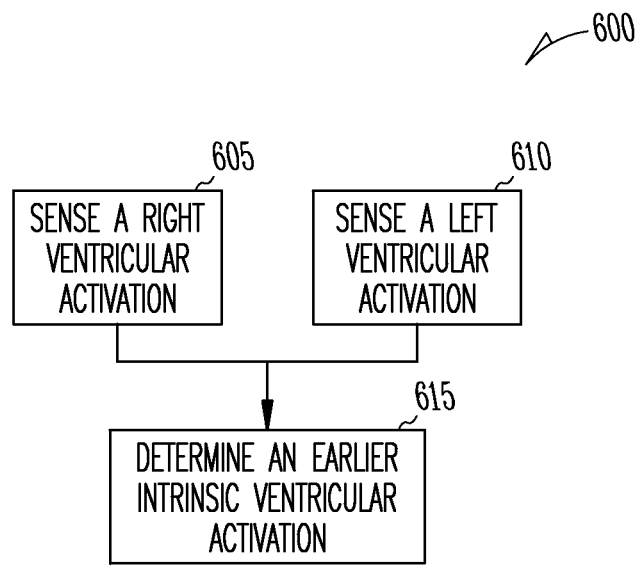
FIG. 6 illustrates generally an example of a method including determining an earlier intrinsic ventricular activation.

FIG. 6 illustrates generally an example of a method 600 including determining an earlier intrinsic ventricular activation.

At 605, a right ventricular intrinsic activation can be sensed. In an example, the right ventricular intrinsic activation can be sensed at a first location of the right ventricle (such as at or near the septal region or the free wall region of the right ventricle). In an example, the right ventricular intrinsic activation can be sensed using the right ventricular sensing channel 10, the lead 15, the electrode 16, and the sense amplifier 11.

At 610, a left ventricular intrinsic activation can be sensed. In an example, the left ventricular intrinsic activation can be sensed at a first location in the left ventricle (such as at or near the free wall region or the septal region of the left ventricle).

In an example, the left ventricular intrinsic activation can be sensed using the left ventricular sensing channel 30, the lead 35, the electrode 36, and the sense amplifier 31.

At 615, an earlier intrinsic ventricular activation can be determined, as between the right and left ventricles during the same cardiac cycle. In an example, the earlier intrinsic ventricular activation can be determined during a first cardiac cycle using information about the sensed right and left ventricular intrinsic activations. In various examples, different methods can be used to determine the earlier and later activation. For example, a processor can monitor a channel receiving left ventricular activation data and right ventricular activation data for the first intrinsic activation following an atrial event and record the corresponding ventricle as the determined earlier intrinsic ventricular activation. In other examples, a processor can be configured to compare sensed intervals from an atrial event (or other common marker) to the right and left ventricle intrinsic activations and determine the earlier intrinsic ventricular activating ventricle from the comparison. In an example, the earlier intrinsic ventricular activation can be determined using the processor 50.

Figure 7:
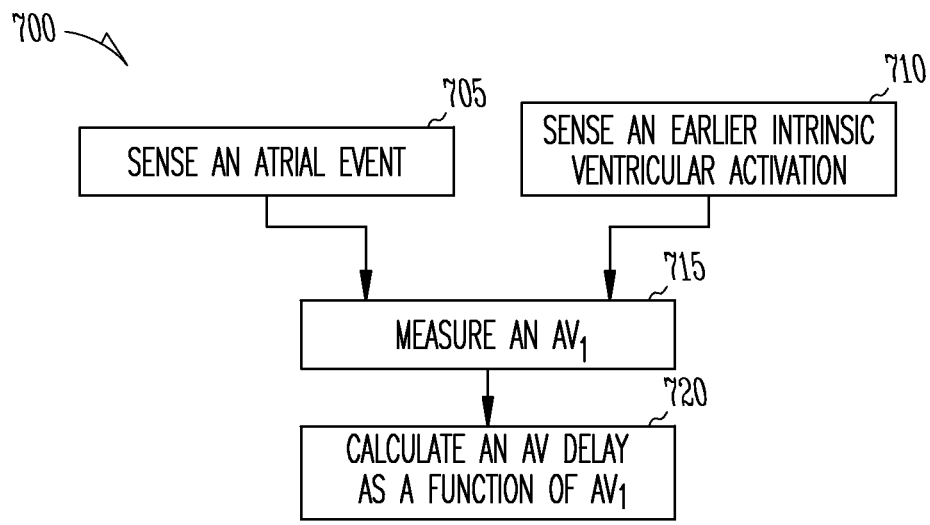
FIG. 7 illustrates generally an example of a method including calculating an AV delay as a function of a determined earlier intrinsic atrioventricular activation ($AV_1$).

FIG. 7 illustrates generally an example of a method 700 including calculating an AV delay as a function of a determined earlier intrinsic atrioventricular activation ($AV_1$).

At 705, an atrial event is sensed. The atrial event can include a right atrial event or a left atrial event. In an example, the atrial event can be sensed using the atrial sensing channel 60, the lead 65, the electrode 66, and the sense amplifier 61.

At 710, an earlier intrinsic ventricular activation ($V_1$) is sensed. In an example, the earlier activating ventricle can be determined such as shown in FIG. 6 or described in method 600.

In an example, the earlier intrinsic ventricular activation can include the right ventricular activation. If so, at 710, an intrinsic right ventricular activation can be sensed as the earlier intrinsic ventricular activation.

In an example, the earlier intrinsic ventricular activation can include the left ventricular activation. If so, at 710, an intrinsic left ventricular activation can be sensed as the earlier intrinsic ventricular activation.

At 715, a determined earlier intrinsic atrioventricular interval $AV_1$ can be measured using the sensed atrial event and the sensed earlier intrinsic ventricular activation. In an example, the $AV_1$ can be measured using the processor 50.

At 720, an AV delay can be calculated as a function of $AV_1$. In certain examples, the determined first ventricular activation can replace the right ventricular activation in any AV delay calculation, or the remaining ventricular activation (e.g., the later intrinsic activation) can replace the left ventricular activation in any AV delay calculation. In an example, the AV delay can be computed as $AVD = k_1 AV_1 + k_2 QRS + k_3$. In other examples, the determined earlier ventricular activation can be substituted for other AV delay calculation parameters.

In Example 1, a system can include an implantable medical device including a processor configured to detect a first occurring intrinsic ventricular activation and to calculate a first AV delay using a first relationship if the first occurring intrinsic ventricular activation includes a right ventricular activation and to calculate a second AV delay using a second relationship if the first occurring intrinsic ventricular activation includes a left ventricular activation.

In Example 2, the first relationship of Example 1 optionally includes $AVD = k_1 AV_R + k_2 \Delta_{RL} + k_3$.

In Example 3, the second relationship of Example 1 optionally includes $AVD = k_1 AV_L + k_2 \Delta_{RL} + k_3$.

In Example 4, a method includes sensing a right ventricular activation, sensing a left ventricular activation, determining an earlier intrinsic ventricular activation using the right ventricular activation and the left ventricular activation, and calculating an AV delay using the earlier intrinsic ventricular activation.

In Example 5, a method includes sensing an atrial event, sensing a first occurring intrinsic ventricular activation, measuring a first occurring atrioventricular ($AV_1$) interval, and calculating an AV delay as a function of the $AV_1$.

AV Delay Calculation Using Paced Atrial Events

In an example, the AV delay can be calculated using an intrinsic atrial event. The present inventor has recognized, among other things, that the AV delay can be calculated using a paced atrial event. In an example, certain subjects can benefit from atrial pacing (e.g., subjects having sick sinus syndrome (SSS), etc.). In an example, the AV delay can be calculated, such as described above, using an interval following a delivered atrial pace ($A_p$) (e.g., $A_p V_L$, $A_p V_R$, etc.) instead of an interval following an intrinsic atrial event. In an example, the atrial pace can be delivered using an atrial pacing channel coupled to a processor (e.g., processor 50), a pulse generator, an atrial lead (e.g., atrial lead 61), and electrode (e.g., electrode 66).

Figure 8:
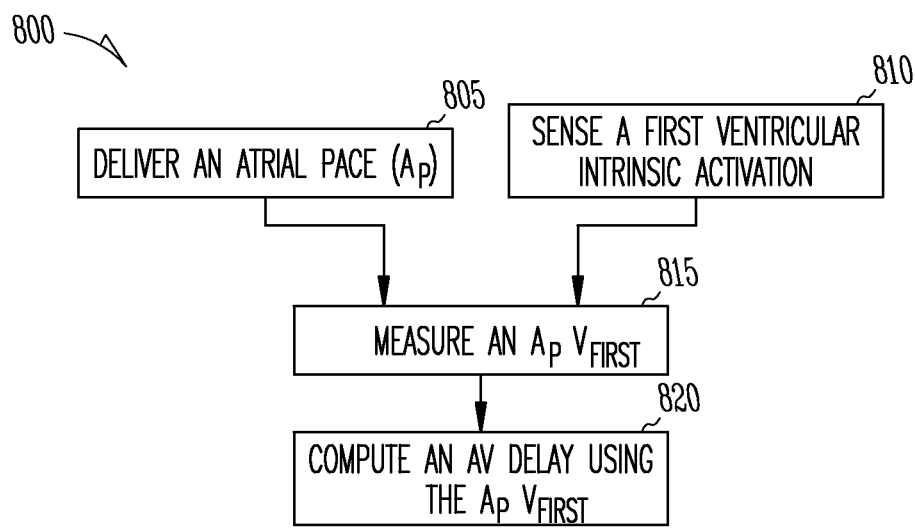
FIG. 8 illustrates generally an example of a method including computing an AV delay using an atrial-paced atrioventricular interval ($A_p V_{first}$).

FIG. 8 illustrates generally an example of a method 800 including computing an AV delay using an atrial-paced atrioventricular interval ($A_p V_{first}$).

At 805, an atrial pace ($A_p$) is delivered. In an example, the atrial pace can be delivered using an atrial pacing channel coupled to a processor (e.g., processor 50), a pulse generator, an atrial lead (e.g., atrial lead 61), and electrode (e.g., electrode 66).

At 810, a first ventricular intrinsic activation ($V_{first}$) is sensed. In an example, the $V_{first}$ can include the intrinsic right ventricular activation, the intrinsic left ventricular activation, an earlier intrinsic activation, or a later intrinsic activation.

At 815, an atrioventricular interval between an $A_p$ and a first ventricular intrinsic activation $V_{first}$ is measured as $A_p V_{first}$. In an example, the $A_p V_{first}$ can include $A_p V_L$. In other examples, the $A_p V_{first}$ can include other timings or intervals, such as $A_p V_R$.

At 820, an AV delay can be computed using the $A_p V_{first}$, such as by substituting $A_p V_{first}$ in for $AV_R$ or $AV_L$ when computing an AV delay (e.g., as shown above).

In Example 1, a system includes an implantable medical device including a processor. The implantable medical device can be configured to deliver an atrial pace and to sense a first ventricular intrinsic activation in response to the delivered atrial pace. The processor can be configured to measure the interval between the atrial pace and the sensed first ventricular intrinsic activation and to compute an AV delay using the measured interval.

In Example 2, a method includes delivering an atrial pace, sensing a first ventricular intrinsic activation, measuring an interval between the delivered atrial pace and the sensed first ventricular intrinsic activation, and computing an AV delay using the measured interval.

Calculating AV Delay Using User-Supplied V-V Timing

In an example, the AV delay can be calculated using an optimal or desired BVO. Generally, an AV delay refers to the time period between an atrial event and a ventricular event. However, in biventricular pacing, both ventricles can be paced. Thus, without specification of an $AV_R$ or $AV_L$, the AV delay typically refers to $AV_R$. The present inventor has recognized, among other things, that it can be advantageous to be able to set the BVO to a user-defined timing (e.g., +20 ms referring to pacing the RV 20 ms before the LV, −20 ms referring to pacing the LV 20 ms before the RV, etc.). Thus, if a user-defined BVO has been set, the AV delay (e.g., the calculated AV delay) can be set to the first activating ventricle as set by the user-defined BVO. Allowing such user input provides for a controllable yet robust pacing system capable of pacing near, at, or beyond clinical norms using clinician or other user-supplied input.

Figure 9:
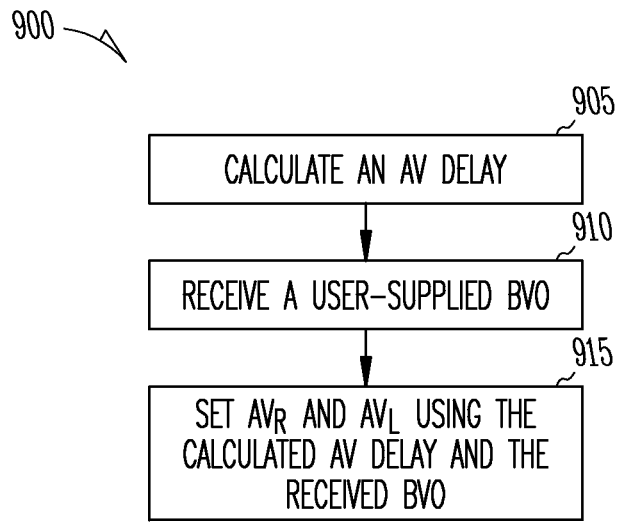
FIG. 9 illustrates generally an example of a method including calculating an AV delay using a user-supplied BVO.

FIG. 9 illustrates generally an example of a method 900 including calculating an AV delay using a user-supplied BVO.

At 905, an AV delay is calculated.

At 910, a user-supplied BVO is received. In an example, the user-supplied BVO can include a clinician-supplied BVO or other user-supplied BVO. In certain examples, the BVO can be received using a combination of at least one of the processor 50, the local user interface 70, or the remote user interface 75.

At 915, an $AV_R$ and $AV_L$ are set using the calculated AV delay and the received user-supplied BVO. In this example, the AV delay is applied to the first activating ventricle, as set by the user-defined BVO. The following illustrates how the $AV_R$ and $AV_L$ can be set using the calculated AV delay (for this illustration, the calculated AV delay is 100 ms) and the user-supplied BVO:

If user-supplied BVO=+20 ms, then $AV_R$=100 ms and the $AV_L$=120 ms.

If user-supplied BVO=+10 ms, then $AV_R$=100 ms and the $AV_L$=110 ms.

If user-supplied BVO=−20 ms, then $AV_R$=120 ms and $AV_L$=100 ms.

If user-supplied BVO=−10 ms, then $AV_R$=110 ms and $AV_L$=100 ms.

If user-supplied BVO=0 ms, then $AV_R$=100 ms and $AV_L$=100 ms.

In other examples, the BVO can correlate to the AV delay. In certain examples, both the AV delay and the BVO can be calculated as a function of the $AV_R$ and the $AV_L$ (e.g., $AVD=k_4 AV_R+k_5 AV_L+k_6$ (as shown above); $BVO=k_7 AV_R+k_8 AV_L+k_9$, wherein the coefficients $k_7$, $k_8$, and $k_9$ can be derived from an analysis of clinical population data relating measured $AV_R$ and $AV_L$ to a desired BVO interval for delivering cardiac resynchronization therapy, and wherein the desired BVO interval can be determined by a measurement of a cardiac function parameter, such as a maximum left ventricular pressure change (dP/dt), arterial pulse pressure, or measurements of cardiac output). Thus, in certain examples, the AV delay can be calculated, adjusted, or otherwise modulated using a clinician or other user-supplied BVO input.

In other examples, the AV delay can be calculated, adjusted, or otherwise modified, using the received BVO. For example, a calculated AV delay can be adjusted proportionally to or adjusted by a portion of the user-supplied BVO using the relationship between the AV delay and the BVO. In other examples, the AV delay can be calculated using the received BVO directly in the AV delay calculation (e.g., $AVD=k_{10} BVO$, where coefficient $k_{10}$ can be derived using clinical population data relating the AVD to the BVO, or $AVD_{new}=AVD_{old}+(k_{11} BVO)$, where coefficient $k_{11}$ can be derived using clinical population data relating the AVD to the BVO).

In Example 1, a system includes an implantable medical device including a processor configured to calculate an AV delay, to receive a user-supplied biventricular offset (BVO), and to set a right atrioventricular delay and a left atrioventricular delay using the calculated AV delay and the received BVO.

In Example 2, a method includes calculating an AV delay, receiving a user-supplied BVO, and setting a right atrioventricular interval and a left atrioventricular interval using the calculated AV delay and the received BVO.

Applying AVD to Follow Earlier Ventricular Pace

As discussed above, the AV delay typically refers to the time period between an atrial event and a right ventricular event. However, the present inventor has recognized, among other things, that it can be advantageous to apply an optimal or desired AV delay (e.g., such as disclosed above) to the earlier activating ventricle (e.g., the RV or the LV, depending on which ventricle is the earlier activating ventricle) rather than to apply the optimal or desired AV delay to the RV by default.

Figure 10:
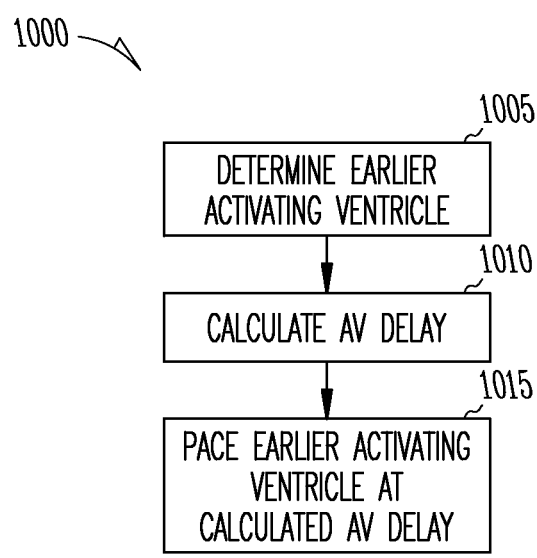
FIG. 10 illustrates generally an example of a method including pacing an earlier activating ventricle at a calculated AV delay.

FIG. 10 illustrates generally an example of a method 1000 including pacing an earlier activating ventricle at a calculated AV delay.

At 1005, an earlier activating ventricle is determined. In an example, the earlier activating ventricle can be determined such as shown in FIG. 6 and described in method 600.

At 1010, an AV delay is calculated.

At 1015, the earlier activating ventricle is paced at the calculated AV delay. In an example, the earlier activating ventricle includes the earlier intrinsic activating ventricle. Thus, whereas in one example of method 900, if the optimal or desired AV delay was calculated to be 100 ms, then the RV would always be paced at 100 ms and the pacing of the LV would be dependent upon the user-supplied BVO, here, at method 1000, if the optimal or desired AV delay was calculated to be 100 ms, then the earlier activating ventricle (whether LV or RV) would be paced at 100 ms and the later activating ventricle would be paced, if at all, at the BVO following the AV delay.

In Example 1, a system includes an implantable medical device including a processor configured to determine a first occurring intrinsic ventricular activation, to calculate an AV delay, and to deliver energy to the first occurring intrinsically activating ventricular at the calculated AV delay.

In Example 2, a method includes determining an earlier intrinsically activating ventricle, calculating an AV delay, and delivering energy to the earlier intrinsically activation ventricle at the calculated AV delay.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventor also contemplates examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system comprising:
   an implantable medical device configured to receive intrinsic cardiac information from a subject, the implantable medical device including:
      an atrial sensing channel configured to receive an intrinsic atrial activation;
      a left ventricular sensing channel configured to receive an intrinsic left ventricular activation; and
      a right ventricular sensing channel configured to receive an intrinsic right ventricular activation; and
   a processor configured to:
      detect any one of: (1) a left intraventricular conduction defect and no right intraventricular conduction defect; (2) no left intraventricular conduction defect and a right intraventricular conduction defect; (3) no left intraventricular conduction defect and no right intraventricular conduction defect; and (4) a left intraventricular conduction defect and a right intraventricular conduction defect, using the intrinsic cardiac information;
      determine a right intrinsic atrioventricular interval, a ventricular depolarization duration, a left intrinsic atrioventricular interval, an interval between an atrial pace and a first ventricular activation, and a detected intrinsic AV interval (AVI);
      calculate a first atrioventricular (AV) delay using at least one of: (1) a function of a right intrinsic atrioventricular interval ($AV_R$) and a ventricular depolarization duration, (2) a function of $AV_R$ and a left intrinsic atrioventricular interval ($AV_L$) and (3) a function of an interval between an atrial pace and a first ventricular activation ($A_pV_{first}$), when detecting the left intraventricular conduction defect or no intraventricular conduction defect; and
      calculate a second AV delay using a function of a detected intrinsic AVI when detecting right intraventricular conduction defect, wherein the intrinsic AVI is the interval between an atrial event and an RV depolarization, an LV depolarization, or the ventricle having the first intrinsic depolarization following the atrial event.

2. The system of claim 1, wherein the relationship between the $AV_R$ and the ventricular depolarization duration (QRS) includes:
   $k_1AV_R+k_2QRS+k_3$, wherein $k_1$, $k_2$, and $k_3$ are coefficients derived from an analysis of clinical population data relating measured $AV_R$, QRS, and a known AV delay.

3. The system of claim 1, wherein the ventricular depolarization duration (QRS) includes at least one of a user-input value including a measured width of a QRS complex or an intrinsic interventricular interval ($\Delta_{RL}$).

4. The system of claim 1, wherein the relationship between the $AV_R$ and the $AV_L$ includes:
   $k_4AV_R+k_5AV_L+k_6$, wherein $k_4$, $k_5$, and $k_6$ are coefficients derived from an analysis of clinical population data relating measured $AV_R$, $AV_L$, and a known AV delay.

5. The system of claim 1, wherein the processor is configured to determine a first occurring intrinsic atrioventricular interval (AVI); and
   wherein the second relationship includes a function of the AVI.

6. The system of claim 5, wherein the function of the AVI includes:
   $k_7 \times AVI$, wherein $k_7$ includes at least one of a user-specified value or a value derived from an analysis of clinical population data relating a measured AVI and a known AV delay.

7. The system of claim 1, wherein the left intraventricular conduction defect includes a left bundle branch block (LBBB) and the right intraventricular conduction defect includes a right bundle branch block (RBBB).

8. The system of claim 1, wherein the intrinsic cardiac information includes at least one of:
   an intrinsic atrioventricular interval ($AV_R$) determined using the received intrinsic atrial activation and the received intrinsic right ventricular activation;
   an intrinsic atrioventricular interval ($AV_L$) determined using the received intrinsic atrial activation and the received intrinsic left ventricular activation;
   a measured width or a duration of a ventricular depolarization (QRS) wave;
   an intrinsic interventricular interval ($\Delta_{RL}$) determined using the received intrinsic left ventricular activation and the received intrinsic right ventricular activation; or
   a first occurring intrinsic atrioventricular interval (AVI) determined using the received intrinsic atrial activation, the received intrinsic left ventricular activation, and the received intrinsic right ventricular activation.

9. The apparatus of claim 1, wherein the first relationship is calculated to pace a first ventricle and the second relationship is calculated to pace a second ventricle.

10. A method comprising:
   receiving intrinsic cardiac information from a subject including an intrinsic atrial activation, an intrinsic left ventricular activation, and an intrinsic right ventricular activation;

detecting by an implantable medical device anyone of: (1) a left intraventricular conduction defect and no right intraventricular conduction defect; (2) no left intraventricular conduction defect and a right intraventricular conduction defect; (3) no left intraventricular conduction defect and no right intraventricular conduction defect; and (4) a left intraventricular conduction defect and a right intraventricular conduction defect; using the intrinsic cardiac information;

determining at least one of a right intrinsic atrioventricular interval, a ventricular depolarization duration, a left intrinsic atrioventricular interval, an interval between an atrial pace and a first ventricular activation, and calculating a first atrioventricular (AV) delay using at least one of: (1) a function of a right intrinsic atrioventricular interval ($AV_R$) and a ventricular depolarization duration, (2) a function of the ($AV_R$) and a left intrinsic atrioventricular interval ($AV_L$) and (3) a function of an interval between an atrial pace and a first ventricular activation ($A_pV_{first}$), when detecting the left intraventricular conduction defect or no intraventricular conduction defect; and determining a detected intrinsic AV interval (AVI) and calculating a second different AV delay using a function of a detected intrinsic AVI when detecting right intraventricular conduction defect, wherein the intrinsic AVI is the interval between an atrial event and an RV depolarization, an LV depolarization, or the ventricle having the first intrinsic depolarization following the atrial event to define the intrinsic AVI.

11. The method of claim 10, wherein the using the relationship between the right intrinsic atrioventricular interval ($AV_R$) and the ventricular depolarization duration (QRS) includes using:

$k_1 AV_R + k_2 QRS + k_3$, wherein $k_1$, $k_2$, and $k_3$ are coefficients derived from an analysis of clinical population data relating measured $AV_R$, QRS, and a known AV delay.

12. The method of claim 10, wherein the using the ventricular depolarization duration (QRS) includes using at least one of a user-input value including a measured width of a QRS complex or an intrinsic interventricular interval ($\Delta_{RL}$).

13. The method of claim 10, wherein the using the relationship between the $AV_R$ and the $AV_L$ includes using:

$k_4 AV_R + k_5 AV_L + k_6$, wherein $k_4$, $k_5$, and $k_6$ are coefficients derived from an analysis of clinical population data relating measured $AV_R$, $AV_L$, and a known AV delay.

14. The method of claim 10, including:
determining a first occurring intrinsic atrioventricular interval (AVI); and
wherein the using the second relationship includes using a function of the AVI.

15. The method of claim 14, wherein the using the function of the AVI includes using:

$k_7 \times AVI$, wherein $k_7$ includes at least one of a user-specified value or a value derived from an analysis of clinical population data relating a measured AVI and a known AV delay.

16. The method of claim 10, wherein the detecting the right intraventricular conduction defect includes detecting a left bundle branch block (LBBB); and
wherein the detecting the left intraventricular conduction defect includes detecting a right bundle branch block (RBBB).

17. The method of claim 10, wherein the using the intrinsic cardiac information includes using at least one of:
an intrinsic atrioventricular interval ($AV_R$) determined using the received intrinsic atrial activation and the received intrinsic right ventricular activation;
an intrinsic atrioventricular interval ($AV_L$) determined using the received intrinsic atrial activation and the received intrinsic left ventricular activation;
a measured width or a duration of a ventricular depolarization (QRS) wave;
an intrinsic interventricular interval ($\Delta_{RL}$) determined using the received intrinsic left ventricular activation and the received intrinsic right ventricular activation; or
a first occurring intrinsic atrioventricular interval (AVI) determined using the received intrinsic atrial activation, the received intrinsic left ventricular activation, and the received intrinsic right ventricular activation.

18. The method of claim 10, wherein the first relationship is used to pace a first ventricle and the second relationship is used to pace a second ventricle.

* * * * *